United States Patent
Park et al.

(10) Patent No.: US 10,631,727 B2
(45) Date of Patent: Apr. 28, 2020

(54) METHOD AND SYSTEM FOR DETECTING TIME DOMAIN CARDIAC PARAMETERS BY USING PUPILLARY RESPONSE

(71) Applicants: SANGMYUNG UNIVERSITY INDUSTRY-ACADEMY COOPERATION FOUNDATION, Jongno-gu, Seoul (KR); CENTER OF HUMAN-CENTERED INTERACTION FOR COEXISTENCE, Seongbuk-gu, Seoul (KR)

(72) Inventors: Sang In Park, Seoul (KR); Dong Won Lee, Seongnam-si (KR); Sungchul Mun, Seoul (KR); Myoung Ju Won, Cheonan-si (KR); Min Cheol Whang, Goyang-si (KR)

(73) Assignees: SANGMYUNG UNIVERSITY INDUSTRY-ACADEMY COOPERATION FOUNDATION, Seoul (KR); CENTER OF HUMAN-CENTERED INTERACTION FOR COEXISTENCE, Seoul (KR)

( * ) Notice: Subject to any disclaimer, the term of this patent is extended or adjusted under 35 U.S.C. 154(b) by 154 days.

(21) Appl. No.: 15/888,430

(22) Filed: Feb. 5, 2018

(65) Prior Publication Data
US 2018/0235464 A1 Aug. 23, 2018

(30) Foreign Application Priority Data

Feb. 17, 2017 (KR) .................. 10-2017-0021521
Nov. 7, 2017 (KR) .................. 10-2017-0147609

(51) Int. Cl.
 A61B 5/00 (2006.01)
 A61B 3/11 (2006.01)
 (Continued)

(52) U.S. Cl.
 CPC ............ *A61B 3/112* (2013.01); *A61B 3/0025* (2013.01); *A61B 3/145* (2013.01); *A61B 5/024* (2013.01);
 (Continued)

(58) Field of Classification Search
 CPC ....... A61B 3/112; A61B 3/0025; A61B 3/145; A61B 5/0402; A61B 5/024;
 (Continued)

(56) References Cited

FOREIGN PATENT DOCUMENTS

KR 10-2017-0004547 A 1/2017
KR 10-2017-0004914 A 1/2017

OTHER PUBLICATIONS

Casolo et al., "Heart Rate Variability During the Acute Phase of Myocardial Infarction", Circulation, Jun. 1992, pp. 2073-2079, vol. 85, No. 6, American Heart Association.
(Continued)

*Primary Examiner* — Scott M. Getzow
(74) *Attorney, Agent, or Firm* — Buchanan Ingersoll & Rooney PC

(57) ABSTRACT

Provided are a method and system for detecting time-domain cardiac information, the method comprising: obtaining moving images of a pupil from a subject; extracting a pupil size variation (PSV) from the moving images; calculating R-peak to R-peak intervals (RRIs) in a predetermined frequency range from the PSV; and obtaining at least one time-domain cardiac parameter by processing the RRIs.

16 Claims, 11 Drawing Sheets

(51) Int. Cl.
| | |
|---|---|
| *A61B 5/024* | (2006.01) |
| *A61B 5/0402* | (2006.01) |
| *A61B 3/14* | (2006.01) |
| *A61B 3/00* | (2006.01) |
| *A61B 5/16* | (2006.01) |

(52) U.S. Cl.
CPC ........ *A61B 5/02444* (2013.01); *A61B 5/0402* (2013.01); *A61B 5/163* (2017.08)

(58) Field of Classification Search
CPC . A61B 5/02405; A61B 2/4035; A61B 2/6821; A61B 5/163; A61B 5/02444; A61B 5/0452; A61B 5/02; A61B 3/10
See application file for complete search history.

(56) References Cited

OTHER PUBLICATIONS

McCraty et al., "Autonomic Assessment Report: A Comprehensive Heart Rate Variability Analysis", HeartMath Research Center, 1996, pp. 1-43, Institute of HeartMath.

Wang et al., "SDNN/RMSSD as a Surrogate for LF/HF: A Revised Investigation", Modelling and Simulation in Engineering, 2012, pp. 1-8, vol. 2012, Hindawi Publishing Corporation.

Vongpatanasin et al., "Effects of Cocaine on Heart Rate Variability in Healthy Subjects", The American Journal of Cardiology, Feb. 1, 2004, pp. 385-388, vol. 93, Excerpta Medica, Inc.

Cohen, "Statistical Power Analysis for the Behavioral Sciences", Biometrics, Sep. 1970, pp. 588, vol. 26, No. 3, International Biometric Society.

Daugman, "How Iris Recognition Works", IEEE Transactions on Circuits and Systems for Video Technology, Jan. 2004, pp. 21-30, vol. 14, No. 1, IEEE.

Dunnett, "A Multiple Comparison Procedure for Comparing Several Treatments with a Control", Journal of the American Statistical Association, Dec. 1955, pp. 1096-1121, vol. 50, No. 272, American Statistical Association.

Lee et al., "Measuring the Degree of Eyestrain Caused by Watching LCD and PDP Devices", International Journal of Industrial Ergonomics, 2009, pp. 798-806, vol. 39, Elsevier B.V.

Heart Rate Variability: Standards of Measurement, Physiological Interpretation, and Clinical Use, ESC/NASPE Task Force, Apr. 1996, 151-181, vol. 1, No. 2.

McCraty et al., "The Coherent Heart Heart-Brain Interactions, Psychophysiological Coherence, and the Emergence of System-Wide Order", Integral Review, Dec. 2009, pp. 10-115, vol. 5, No. 2, HeartMath Research Center.

Park et al., "Does Visual Fatigue from 3D Displays Affect Autonomic Regulation and Heart Rhythm?", International Journal of Psychophysiology, 2014, pp. 42-48, vol. 92, Elsevier B.V.

Russell, "A Circumplex Model of Affect", Journal of Personality and Social Psychology, 1980, pp. 1161-1178, vol. 39, No. 6, American Psychological Association, Inc.

Office Action dated Mar. 6, 2019, by the Korean Intellectual Property Office in corresponding Korean Patent Application No. 10-2017-0147609. (34 pages).

US 10,631,727 B2

METHOD AND SYSTEM FOR DETECTING TIME DOMAIN CARDIAC PARAMETERS BY USING PUPILLARY RESPONSE

CROSS-REFERENCE TO RELATED APPLICATION

This application claims the benefit of Korean Patent Application Nos. 10-2017-0021521, filed on Feb. 17, 2017, and 10-2017-0147609, filed on Nov. 7, 2017, in the Korean Intellectual Property Office, the disclosures of which are incorporated herein in their entirety by reference.

BACKGROUND

1. Field

One or more embodiments relate to a method of detecting physiological information by using a pupillary response, and a system using the method, and more particularly, to method of detecting time-domain cardiac parameters from a pupil size variation, and a system using the method.

2. Description of the Related Art

In vital signal monitoring (VSM), physiological information can be acquired by a sensor attached to a human body. Such physiological information includes electrocardiogram (ECG), photo-plethysmograph (PPG), blood pressure (BP), galvanic skin response (GSR), skin temperature (SKT), respiration (RSP) and electroencephalogram (EEG).

The heart and brain are two main organs of the human body and analysis thereof provide the ability to evaluate human behavior and obtain information that may be used in response to events and in medical diagnosis. The VSM may be applicable in various fields such as ubiquitous healthcare (U-healthcare), emotional information and communication technology (e-ICT), human factor and ergonomics (HF&E), human computer interfaces (HCIs), and security systems.

Regarding ECG and EEG, sensors attached to the body are used to measure physiological signals and thus, may cause inconvenience to patients. That is, the human body experiences considerable stress and inconvenience when using sensors to measure such signals. In addition, there are burdens and restrictions with respect to the cost of using the attached sensors and to the movement of the subject, due to attached sensor hardware.

Therefore, VSM technology is required in the measurement of physiological signals by using non-contact, non-invasive, and non-obtrusive methods while providing unfettered movement at low cost.

Recently, VSM technology has been incorporated into wireless wearable devices allowing for the development of portable measuring equipment. These portable devices can measure heart rate (HR) and RSP by using VSM embedded into accessories such as watches, bracelets, or glasses.

Wearable device technology is predicted to develop from portable devices to "attachable" devices shortly. It is also predicted that attachable devices will be transferred to "edible" devices.

VSM technology has been developed to measure physiological signals by using non-contact, non-invasive, and non-obtrusive methods that provide unfettered movement at low cost. While VSM will continue to advance technologically, innovative vision-based VSM technology is required to be developed also.

SUMMARY

One or more embodiments include a system and method for inferring and detecting human vital signs by using a non-invasive and non-obstructive method at low cost.

In detail, one or more embodiments include a system and method for detecting time-domain cardiac parameters by using a pupillary response or pupil size variation.

Additional aspects will be set forth in part in the description which follows and, in part, will be apparent from the description, or may be learned by practice of the presented embodiments.

According to one or more exemplary embodiments, the method of detecting time-domain cardiac parameters, the method comprises obtaining moving images of a pupil from a subject; extracting a pupil size variation (PSV) from the moving images; calculating R-peak to R-peak intervals (RRI) in a predetermined frequency range from the PSV; and obtaining at least one time-domain cardiac parameter by processing the RRI.

According to one or more exemplary embodiments, a system adopting the method of claim 1, the system comprising: a video capturing unit configured to capture the moving images of the subject; and a computer architecture based analyzing unit, including analysis tools and configured to process and analyze the moving images, and calculate the at least one cardiac parameter.

According to one or more exemplary embodiments, the predetermined frequency range is a harmonic frequency range of 1/100 of the frequency range of an electrocardiogram (ECG) signal obtained by sensors.

According to one or more exemplary embodiments, the predetermined frequency range is between 0.005 Hz-0.012 Hz.

According to one or more exemplary embodiments, the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

BRIEF DESCRIPTION OF THE DRAWINGS

In these and/or other aspects will become apparent and more readily appreciated from the following description of the embodiments, taken in conjunction with the accompanying drawings in which.

DETAILED DESCRIPTION

Figure 1:
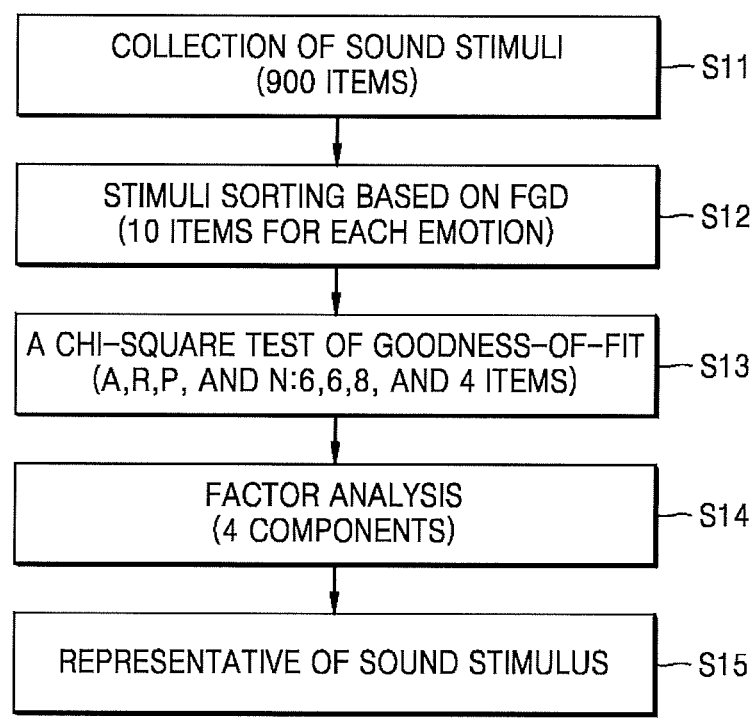
FIG. 1 shows a procedure for selecting a representative of sound stimuli used in an example test, according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, a method and system for inferring and detecting physiological signals according to the present inventive concept is described with reference to the accompanying drawings.

The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. Like reference numerals in the drawings denote like elements. In the drawings, elements and regions are schematically illustrated. Accordingly, the concept of the invention is not limited by the relative sizes or distances shown in the attached drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, numbers, steps, operations, elements, and/or components, but do not preclude the presence or addition of one or more other features, numbers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present application, and will not be interpreted in an overly formal sense unless expressly so defined herein.

The embodiments described below involve processing time-domain cardiac parameters from a pupillary response which is obtained from video information.

The present invention, which may be sufficiently understood through the embodiments described below, involve extraction of time-domain cardiac information of a heart from the pupillary response or pupil size variation by using a vision system equipped with a video camera such as a webcam without any physical restriction or psychological pressure on the subject. In particular, the pupillary response is detected from the image information and time-domain cardiac parameters are extracted from the detected pupillary response.

In the experiment of the present invention, the reliability of the time-domain cardiac parameters extracted from the pupil size variation (PSV) acquired through moving images was compared with the ground truth signal by ECG sensors.

Experiments in relation to the present invention were performed by using video equipment, and a computer architecture based analyzing system for processing and analyzing the moving images, which included analysis tools provided by software. The system according to exemplary embodiments was developed using Visual C++ 2010 and OpenCV 2.4.3. The signal processing function for fast Fourier transformation (FFT), band-pass filter (BPF), etc. was provided by LabVIEW 2010.

Experimental Stimuli

In order to cause variations in a physiological state, this experiment used sound stimuli based on the Russell's circomplex model (Russell, 1980). The sound stimuli included a plurality of factors, including arousal, relaxation, positive, negative, and neutral sounds. The neutral sound was defined by an absence of acoustic stimulus. The steps for selecting sound stimuli are shown in FIG. 1 and listed as follows:

(S11) Nine hundred sound sources were collected from the broadcast media such as advertisements, dramas, and movies.

(S12) The sound sources were then categorized into four groups (i.e., arousal, relaxation, positive, and negative). Each group was comprised of 10 commonly selected items based on a focus group discussion for a total of forty sound stimuli.

(S13) These stimuli were used to conduct surveys for suitability for each emotion (i.e., A: arousal, R: relaxation, P: positive, and N: negative) based on data gathered from 150 subjects that were evenly split into 75 males and 75 females. The mean age was 27.36 years±1.66 years. A subjective evaluation was required to select each item for the four factors, which could result in duplicates of one or more of the items.

(S14) A chi-square test for goodness-of-fit was performed to determine whether each emotion sound was equally preferred. Preference for each emotion sound was equally distributed in the population (arousal: 6 items, relaxation: 6 items, positive: 8 items, and negative: 4 items) as shown in Table 1.

Table 1 shows the chi-square test results for goodness-of-fit in which the items selected for each emotion are based on comparisons of observation and expectation values.

TABLE 1

|  | N | Chi-Square | Sig. |
| --- | --- | --- | --- |
| Arousal | | | |
| arousal 1 | 150 | 83.867 | .000 |
| arousal 2 | 150 | 45.573 | .000 |
| arousal 3 | 150 | 58.200 | .000 |
| arousal 5 | 150 | 83.440 | .000 |
| arousal 9 | 150 | 10.467 | .000 |
| arousal 10 | 150 | 70.427 | .000 |
| Relaxation | | | |
| relaxation 1 | 150 | 131.120 | .000 |
| relaxation 2 | 150 | 163.227 | .000 |
| relaxation 5 | 150 | 80.720 | .000 |
| relaxation 6 | 150 | 11.640 | .000 |
| relaxation 7 | 150 | 82.587 | .000 |
| relaxation 10 | 150 | 228.933 | .000 |

TABLE 1-continued

|  | N | Chi-Square | Sig. |
|---|---|---|---|
| Positive | | | |
| positive 2 | 150 | 35.040 | .000 |
| positive 3 | 150 | 90.533 | .000 |
| positive 4 | 150 | 101.920 | .000 |
| positive 5 | 150 | 66.040 | .000 |
| positive 7 | 150 | 143.813 | .000 |
| positive 8 | 150 | 128.027 | .000 |
| positive 9 | 150 | 47.013 | .000 |
| positive 10 | 150 | 138.053 | .000 |
| Negative | | | |
| negative 1 | 150 | 119.920 | .000 |
| negative 2 | 150 | 59.440 | .000 |
| negative 5 | 150 | 117.360 | .000 |
| negative 9 | 150 | 62.080 | .000 |

Resurveys of the sound stimuli were conducted in relation to each emotion from the 150 subjects by using a seven-point scale based on 1 indicating strong disagreement to 7 indicating strong agreement.

Valid sounds relating to each emotion were analyzed using principal component analysis (PCA) based on Varimax (orthogonal) rotation. The analysis yielded four factors explaining the variance for the entire set of variables. After obtaining the analysis results, representative sound stimuli for each emotion were derived, as shown in Table 2.

In Table 2, the bold type is the same factor, the blur character is the communalities <0.5, and the thick, light gray lettering with shading in the background represents the representative acoustic stimulus for each emotion.

TABLE 2

|  | Component | | | |
|---|---|---|---|---|
|  | 1 | 2 | 3 | 4 |
| positive 9 | .812 | .065 | .021 | −.033 |
| arousal 9 | .751 | −.353 | −.157 | .107 |
| relaxation 7 | .717 | .355 | .084 | .133 |
| positive 2 | .531 | −.202 | .203 | .107 |
| positive 3 | −.528 | .222 | .406 | −.003 |
| positive 8 | .520 | .142 | .161 | .074 |
| relaxation 2 | .192 | .684 | .109 | .004 |
| relaxation 1 | .028 | .649 | .168 | −.147 |
| relaxation 5 | −.290 | .629 | −.008 | .132 |
| relaxation 6 | .025 | .628 | −.061 | .107 |
| relaxation 10 | .052 | .569 | −.320 | −.187 |
| arousal 10 | −.201 | .529 | −.111 | .409 |
| positive 10 | −.145 | .424 | .342 | −.020 |
| negative 1 | −.257 | −.009 | .672 | .123 |
| positive 4 | .111 | .096 | .608 | −.185 |
| negative 2 | −.503 | .108 | .580 | .104 |
| negative 9 | .289 | −.252 | .566 | −.051 |
| negative 5 | .216 | −.232 | .528 | −.094 |
| positive 5 | .377 | .014 | .439 | −.019 |
| positive 7 | .002 | .193 | .403 | .128 |
| arousal 1 | −.158 | .209 | −.042 | .774 |
| arousal 2 | .129 | −.049 | .015 | .765 |
| arousal 5 | .210 | −.043 | .097 | .672 |
| arousal 3 | .566 | −.159 | −.140 | .617 |

Experimental Procedure

Seventy undergraduate volunteers of both genders, evenly split between males and females, ranging in age from 20 to 30 years old with a mean of 24.52 years±0.64 years participated in this experiment. All subjects had normal or corrected-to-normal vision (i.e., over 0.8), and no family or medical history of disease involving visual function, cardiovascular system, or the central nervous system. Informed written consent was obtained from each subject prior to the study. This experimental study was approved by the Institutional Review Board of Sangmyung University, Seoul, South Korea (2015 Aug. 1).

The experiment was composed of two trials where each trail was conducted for a duration of 5 min. The first trail was based on the movelessness condition (MNC), which involves not moving or speaking. The second trial was based on a natural movement condition (NMC) involving simple conversations and slight movements. Participants repeatedly conducted the two trials and the order was randomized across the subjects. In order to verify the difference of movement between the two conditions, this experiment quantitatively measured the amount of movement during the experiment by using webcam images of each subject. In the present invention, the moving image may include at least one pupil, that is, one pupil or both pupils image.

The images were recorded at 30 frames per second (fps) with a resolution of 1920×1080 by using a HD Pro C920 camera from Logitech Inc. The movement measured the upper body and face based on MPEG-4 (Tekalp and Ostermann, 2000; JPandzic and Forchheimer, 2002). The movement in the upper body was extracted from the whole image based on frame differences. The upper body line was not tracking because the background was stationary.

The movement in the face was extracted from 84 MPEG-4 animation points based on frame differences by using visage SDK 7.4 software from Visage Technologies Inc. All movement data used the mean value from each subject during the experiment and was compared to the difference of movement between the two trails, as shown in FIG. 2.

Figure 2:
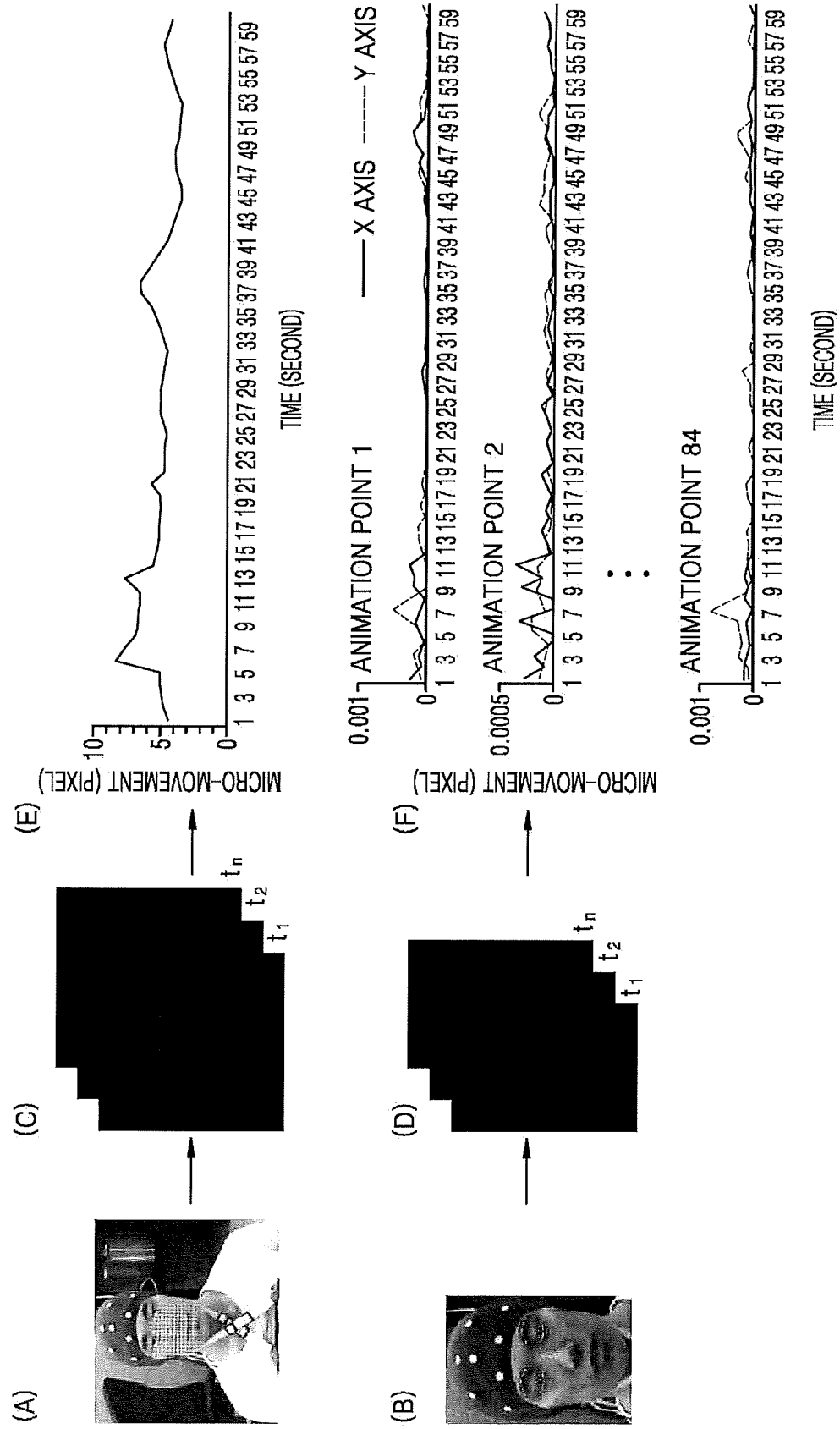
FIG. 2 shows an experimental procedure for measuring the amount of movement in an upper body, according to one or more embodiments.

FIG. 2 shows an example of measuring the amount of motion of the subject's upper body in a state of the face is located at the intersection of the X axis and the Y axis.

In FIG. 2, (A) is an upper body image, (B) is a tracked face image at 84 MPEG-4 animation points, (C) and (D) shows the difference between before and after frames, (E) is a movement signal from the upper body, and (F) shows movement signals from 84 MPEG-4 animation points.

In order to cause the variation of physiological states, sound stimuli were presented to the participants during the trails. Each sound stimulus was randomly presented for 1 min for a total of five stimuli over the 5 min trial. A reference stimulus was presented for 3 min prior to the initiation of the task. The detailed experimental procedure is shown in FIG. 3.

Figure 3:
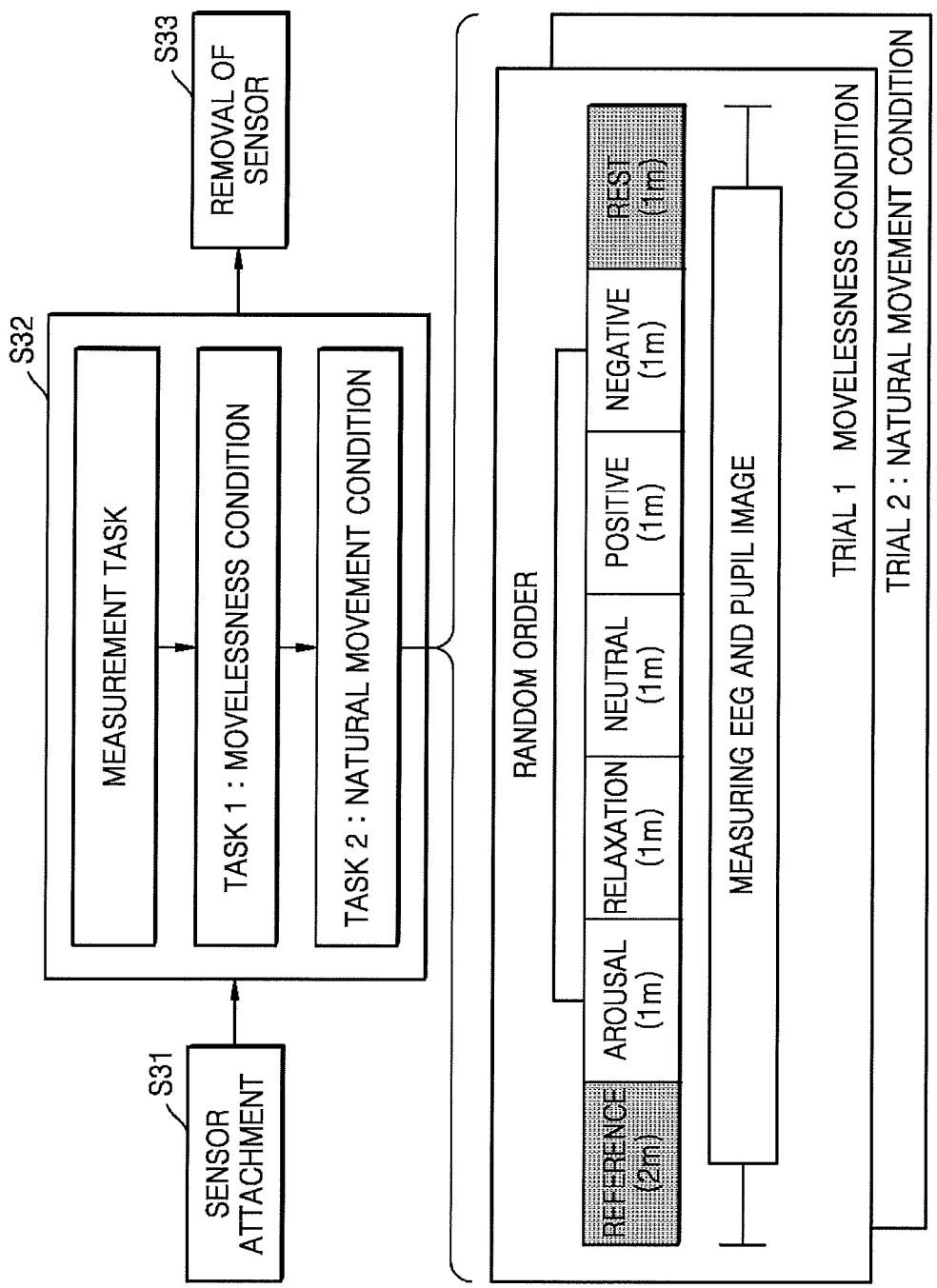
FIG. 3 is a block diagram for explaining an experimental procedure, according to one or more embodiments.

The experimental procedure includes the sensor attachment S31, the measurement task S32 and the sensor removal S33 as shown in FIG. 3, and the measurement task S32 proceed as follows.

The experiment was conducted indoors with varying illumination caused by sunlight entering through the windows. The participants gazed at a black wall at a distance of 1.5 m while sitting in a comfortable chair. Sound stimuli were equally presented in both the trials by using earphones. The subjects were asked to constrict their movements and speaking during the MNC trial. However, the NMC trial involved a simple conversation and slight movement by the subjects. The subjects were asked to introduce themselves to another person as part of the conversation for sound stimuli thereby involving feelings and thinking of the sound stimuli. During the experiment, an ECG signal and pupil image data were obtained.

ECG signals were sampled and recorded at a 500 Hz sampling rate through one channel with the lead-I method by an amplifier system including ECG 100C amplifiers and a MP100 power supply from BIOPAC System Inc. The ECG signals were digitized by a NI-DAQ-Pad 9205 of National Instrument Inc.

Pupil images were recorded at 125 fps with a resolution of 960×400 by GS3-U3-23S6M-C infrared camera from Point Grey Research Inc.

Hereinafter, a method for extracting or constructing (recovering) vital signs from a pupillary response will be described.

Extraction of a Papillary Response

The pupil detection procedure acquires moving images using the infrared video camera system as shown in FIG. 12, and then requires a specific image processing procedure.

Figure 4:
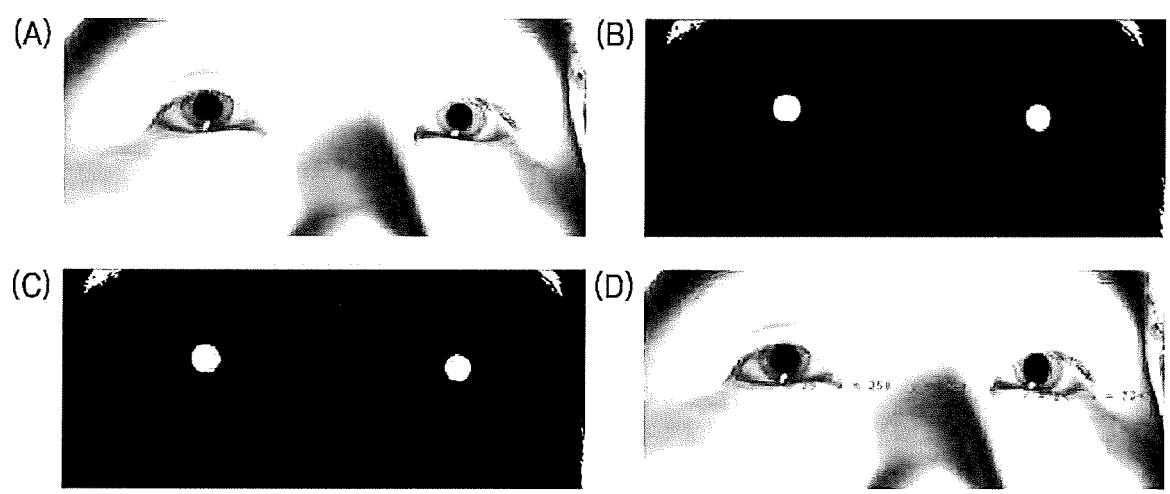
FIG. 4 shows a procedure for detecting a pupil region, according to one or more embodiments.

The pupil detection procedure may require following certain image processing steps since the images were captured using an infrared video camera, as shown in FIG. 4.

FIG. 4 shows a process of detecting a pupil region from the face image of a subject. In FIG. 4, (A) shows an input image (gray scale) obtained from a subject, (B) shows a binarized image based on an auto threshold, (C) shows pupil positions by the circular edge detection, and (D) shows the real-time detection result of the pupil region including the information about the center coordinates and the diameter of the pupil region. The threshold value was defined by a linear regression model that used a brightness value of the whole image, as shown in Equation 1.

$$\text{Threshold} = (-0.118 \times B_{mean} + 1.051 \times B_{max}) + 7.973B = \text{Brightness value} \quad \langle\text{Equation 1}\rangle$$

The next step to determine the pupil position involved processing the binary image by using a circular edge detection algorithm, as shown in Equation 2 (Daugman, 2004; Lee et al., 2009).

$$\text{Max}_{(r,x_0,y_0)} \left| G\sigma(r) * \frac{\delta}{\delta r} \oint_{r,x_0,y_0} \frac{I(x,y)}{2\pi r} ds \right| \quad \langle\text{Equation 2}\rangle$$

$I(x, y)$ = a grey level at the $(x, y)$ position $(x_0, y_0)$ = center position of pupil $r$ = radius of pupil In case that multiple pupil positions are selected, the reflected light caused by the infrared lamp may be used. Then an accurate pupil position was obtained, including centroid coordinates (x, y) and a diameter.

Pupil diameter data (signal) was resampled at a frequency range of 1 Hz-30 Hz, as shown in Equation 3. The resampling procedure for the pupil diameter data involved a sampling rate of 30 data points, which then calculated the mean value during 1-s intervals by using a common sliding moving average technique (i.e., a window size of 1 second and a resolution of 1 second). However, non-tracked pupil diameter data caused by the eye closing was not involved in the resampling procedure.

$$(SMA_m)_{x+n} = \left(\frac{\sum_{i=1}^{m} P_i}{m}\right)_x, \left(\frac{\sum_{i=1}^{m} P_i}{m}\right)_{x+1}, \ldots, \left(\frac{\sum_{i=1}^{m} P_i}{m}\right)_{x+n} \quad \langle\text{Equation 3}\rangle$$

$SMA$ = sliding moving average $P$ = pupil diameter

Detecting Time-Domain Index in Cardiac Activity

Figure 5:
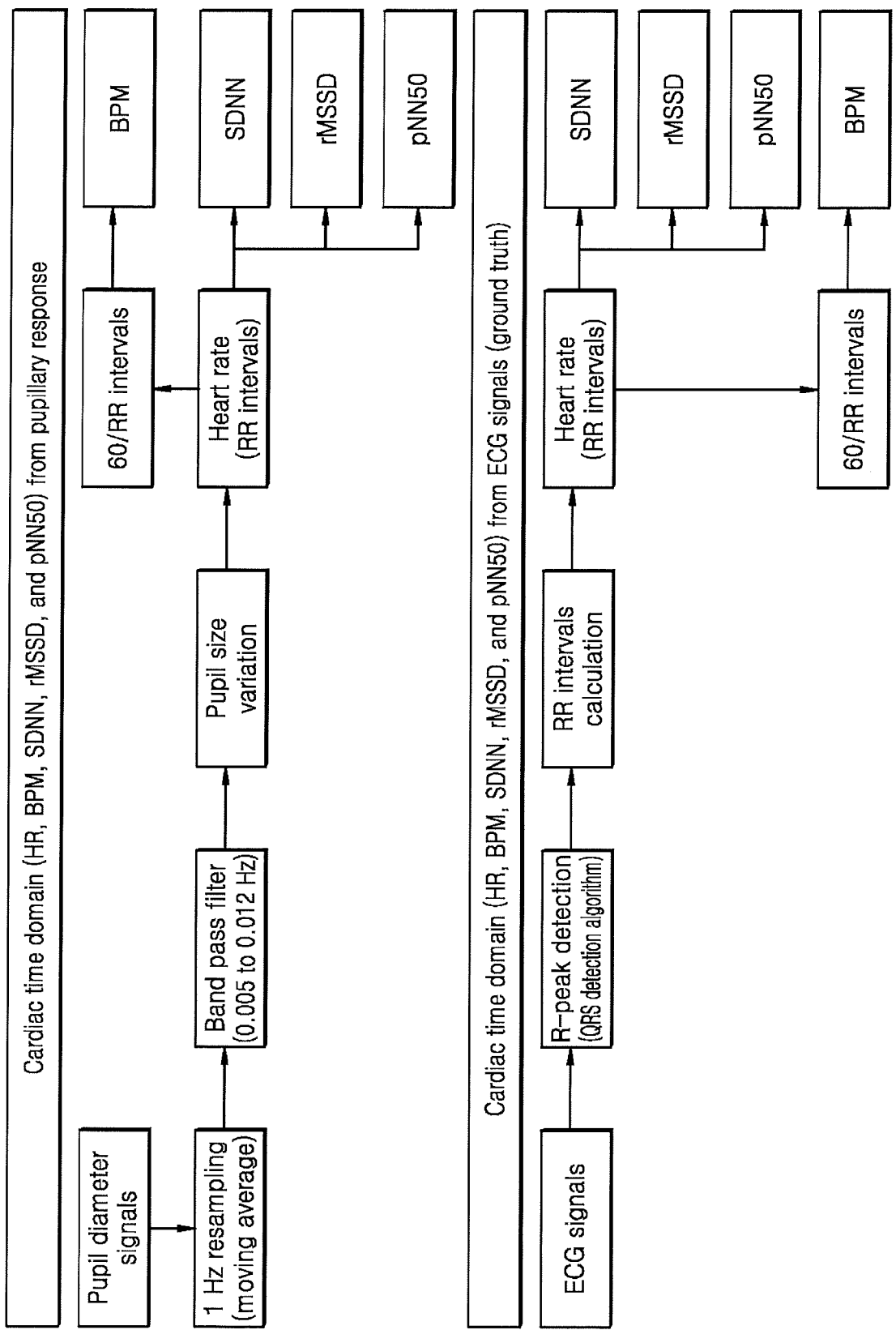
FIG. 5 schematically shows processes of obtaining time-domain cardiac parameters from pupil moving images (pupil diameter signals) and electrocardiogram (ECG) signals.

The detections of the cardiac time-domain indexes (parameters) are now described along with FIG. 5. Referring FIG. 5, the parameters of cardiac time-domain include HR, SDNN, rMSSD and pNN50 which is determined and obtained from the pupillary response, and ECG signal (ground truth).

The HR is the interval of heartbeat and is related to the speed of heartbeat. The BPM is the number of heartbeats for 1 min. It is calculated from the 60 R-peak to R-peak intervals (RRI). The SDNN is the standard deviation of the normal to normal intervals of the R-R intervals. It reflects the ebb and flow of the heart's intrinsic function. This measure is indicator of left ventricular dysfunction, peak creatine kinase levels, Killip class, and sudden cardiac death (Casole et al., 1992; McCraty and Atkinson, 1996; Wang and Huang, 2012; Park et al., 2014). The SDNN is highly depressed below 50 ms, and moderately depressed above 100 ms (McCraty and Atkinson, 1996).

The rMSSD is the square root of the mean of the squares of successive normal RR intervals. This measure reflects the high frequency (short-term variance) in heart rate variability (HRV), and is an indicator of the regulation of the parasympathetic nervous system (vagal break) in the heart (McCraty and Atkinson, 1996; Wang and Huang, 2012; Park et al., 2014).

The pNN50 is the percent (proportion) of successive normal RR intervals that differ by more than 50 ms. This measure is closely correlated with a high frequency in the HRV and is an indicator of parasympathetic nervous system control of the HR (Vongpatanasin, et al., 2004; Wang and Huang, 2012).

The resampled pupil diameter data at 1 Hz was processed by the band pass filter (BPF) of 0.005 Hz to 0.012 Hz in order to ensure the information was relevant to heart, as shown in Equation (4).

$$|A(j\omega)| = \frac{\omega_0 \omega}{\sqrt{(\omega_0^2 - \omega^2)^2 + 9\omega^2 \omega_0^2}} \quad \langle\text{Equation 4}\rangle$$

The BPF uses a low pass filter and a high pass filter based on the Butterworth filter provided by Labview 2010 (Bogdan, M., & Panu, M. LabVIEW modeling and simulation, of the digital filters—In Engineering of Modern Electric Systems, 2015 IEEE).

The BPF range of 0.5 Hz-1.2 Hz was related to the cardiac flow and applied by the harmonic frequency with a 1/100 resolution. Then the filtered data may be calculated using the PSV based on the frame difference of the pupil diameter. The HR was calculated from the mean value of the PSV signals, as shown in Equation (5). The HR means the speed of the heartbeat was controlled by the ANS as calculated from the RRI in ECG signals (Malik, 1996; McCraty et al., 2009; Park et al., 2014). This procedure may be performed or processed by a sliding window technique (i.e., a window size of 30 s and a resolution of 1 s).

$$PSV = \frac{\sum_{i=1}^{n} |P_{n+1} - P_n|}{n} \quad \langle\text{Equation 5}\rangle$$

$PSV$ = pupil size variation $P$ = pupil diameter

Other cardiac time domain indexes, such as SDNN, rMSSD, and pNN50, may be extracted from the RRI signals. The SDNN can be calculated from the standard deviation of the RRI signals based on a normal range of 0.5 Hz to 1.2 Hz. The rMSSD can be calculated from the square root of the mean of the squares of RRI signals with a normal range. The pNN50 can be calculated from counted number of RR intervals that differ by more than 50 ms (Wang and Huang, 2012), as shown in Equation (6).

$$SDNN = \sqrt{\frac{1}{N-1}\sum_{n=2}^{N}[X(n)-X]^2}$$

$$rMSSD = \sqrt{\frac{1}{N-2}\sum_{n=3}^{N}[X(n)-X(n-1)]^2}$$

$$pNN50 = \frac{NN < 50 \text{ count}}{\text{total } NN \text{ count}}$$

(Equation 6)

The ECG signals of Lead-I may be recorded at a 500 Hz sampling rate and are processed by the BPF of 0.5 Hz 0.12 Hz. The R-peak may be extracted from this recording by using the QRS detection algorithm as discussed by Pan and Tompkins (1985). The RRIs are the interval measured from R-peak to R-peak intervals. SDNN, rMSSD, and pNN50 can be calculated from Equation (6) based on the pupil data as mentioned in the above. The detailed procedure for processing the ECG signals is shown in FIG. 5 showing a procedure of signal processing of cardiac time index.

Result

The pupillary response was processed to extract the vital signs from the cardiac time domain index, cardiac frequency domain index, EEG spectral index, and the HEP index of the test subjects. These components were compared with each index from the sensor signals (i.e., ground truth) based on correlation coefficient (r) and mean error value (ME). The data was analyzed with respect to both MNC and NMC for the test subjects.

To verify the difference of the amount movement between the two conditions of MNC and NMC, the movement data was quantitatively analyzed. The movement data was a normal distribution based on a normality test of probability-value (p)>0.05, and from an independent t-test. A Bonferroni correction was performed for the derived statistical significances (Dunnett, 1955). The statistical significance level was controlled based on the number of each individual hypothesis (i.e., $\alpha=0.05/n$). The statistical significant level of the movement data sat up 0.0167 (upper body, X and Y axis in face, $\alpha=0.05/3$). The effect size based on Cohen's d was also calculated to confirm practical significance. In Cohen's d, standard values of 0.10, 0.25, and 0.40 for effect size are generally regarded as small, medium, and large, respectively (Cohen, 2013).

Figure 6:
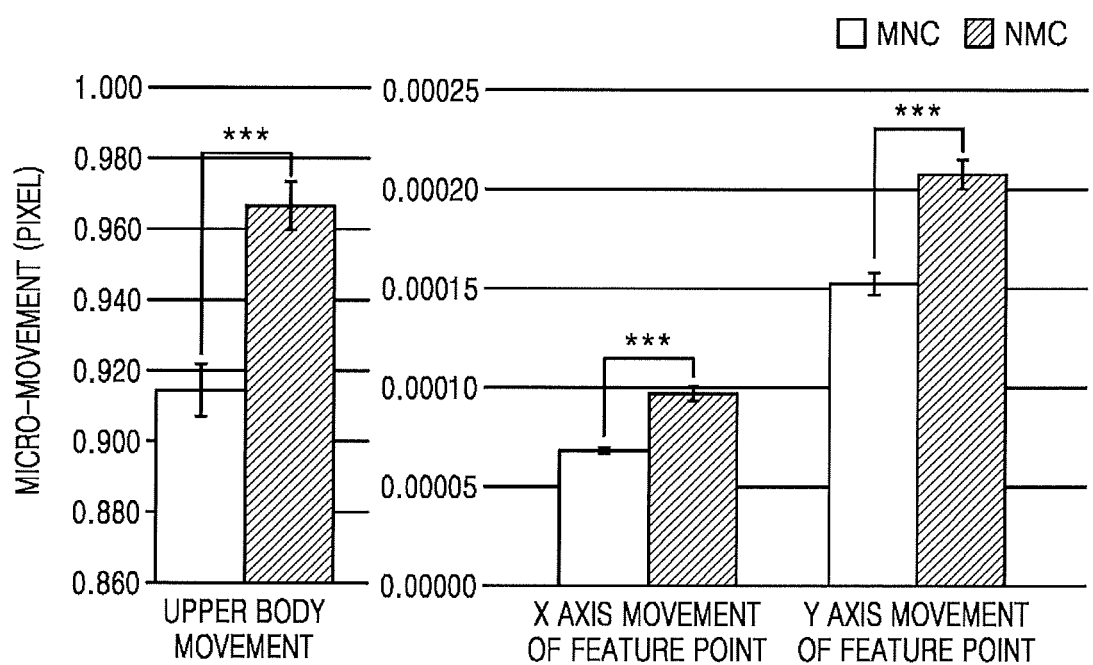
FIG. 6 shows a sample of averages of amount movement in upper body.

FIG. 6 shows averages of amount movement in upper body, X and Y axis in face for MNC and NMC (n=140, ***p<0.001) of one subject. Table 3 shows all subjects data of amount movement in upper body, X and Y axis in face for MNC and NMC.

Referring FIG. 6 and Table 3 according to the analysis, the amount of movement in MNC (upper body, X and Y axis for the face) are significantly increased compared to the NMC for the upper body (t(138)=-5.121, p=0.000, Cohen's d=1.366 with large effect size), X axis for the face (t(138)=-6.801, p=0.000, Cohen's d=1.158 with large effect size), and Y axis for the face (t(138)=-6.255, p=0.000, Cohen's d=1.118 with large effect size).

TABLE 3

| Subjects | Movelessness Condition (MNC) | | | Natural Movement Condition (NMC) | | |
| --- | --- | --- | --- | --- | --- | --- |
| Subjects | Upper body | X axis | Y axis | Upper body | X axis | Y axis |
| S1 | 0.972675 | 0.000073 | 0.000158 | 1.003305 | 0.000117 | 0.000237 |
| S2 | 0.961020 | 0.000081 | 0.000170 | 1.002237 | 0.000101 | 0.000243 |
| S3 | 0.942111 | 0.000071 | 0.000206 | 0.945477 | 0.000081 | 0.000220 |
| S4 | 0.955444 | 0.000067 | 0.000189 | 0.960506 | 0.000072 | 0.000191 |
| S5 | 0.931979 | 0.000056 | 0.000106 | 0.972033 | 0.000070 | 0.000153 |
| S6 | 0.910416 | 0.000057 | 0.000103 | 0.999692 | 0.000086 | 0.000174 |
| S7 | 0.862268 | 0.000055 | 0.000216 | 0.867949 | 0.000071 | 0.000249 |
| S8 | 0.832109 | 0.000056 | 0.000182 | 0.884868 | 0.000068 | 0.000277 |
| S9 | 0.890771 | 0.000099 | 0.000188 | 0.890783 | 0.000099 | 0.000242 |
| S10 | 0.869373 | 0.000073 | 0.000168 | 0.872451 | 0.000089 | 0.000206 |
| S11 | 0.908724 | 0.000057 | 0.000128 | 0.963280 | 0.000102 | 0.000187 |
| S12 | 0.954168 | 0.000091 | 0.000180 | 0.964322 | 0.000181 | 0.000190 |
| S13 | 0.846164 | 0.000070 | 0.000144 | 0.917798 | 0.000079 | 0.000172 |
| S14 | 0.953219 | 0.000062 | 0.000116 | 1.024050 | 0.000093 | 0.000185 |
| S15 | 0.936300 | 0.000068 | 0.000202 | 0.952505 | 0.000101 | 0.000287 |
| S16 | 0.943040 | 0.000077 | 0.000220 | 0.958412 | 0.000106 | 0.000308 |
| S17 | 0.852292 | 0.000099 | 0.000199 | 0.901039 | 0.000077 | 0.000310 |
| S18 | 0.901182 | 0.000082 | 0.000278 | 0.920493 | 0.000084 | 0.000262 |
| S19 | 0.943810 | 0.000075 | 0.000156 | 0.974675 | 0.000099 | 0.000386 |
| S20 | 0.988983 | 0.000070 | 0.000162 | 1.029716 | 0.000175 | 0.000184 |
| S21 | 0.952451 | 0.000065 | 0.000102 | 1.005191 | 0.000081 | 0.000141 |
| S22 | 0.965017 | 0.000064 | 0.000099 | 0.999090 | 0.000183 | 0.000150 |
| S23 | 1.068848 | 0.000101 | 0.000200 | 1.090858 | 0.000108 | 0.000255 |
| S24 | 0.993841 | 0.000092 | 0.000184 | 1.052424 | 0.000111 | 0.000247 |
| S25 | 0.883615 | 0.000064 | 0.000258 | 0.913927 | 0.000077 | 0.000283 |
| S26 | 0.870531 | 0.000051 | 0.000221 | 0.906540 | 0.000074 | 0.000252 |
| S27 | 0.955718 | 0.000064 | 0.000126 | 0.963460 | 0.000071 | 0.000169 |
| S28 | 0.968524 | 0.000061 | 0.000142 | 0.985782 | 0.000075 | 0.000184 |
| S29 | 0.794718 | 0.000067 | 0.000119 | 0.918873 | 0.000074 | 0.000136 |
| S30 | 0.817818 | 0.000064 | 0.000105 | 0.914591 | 0.000073 | 0.000148 |
| S31 | 0.937005 | 0.000053 | 0.000138 | 0.979654 | 0.000080 | 0.000203 |

TABLE 3-continued

| Subjects | Movelessness Condition (MNC) | | | Natural Movement Condition (NMC) | | |
|---|---|---|---|---|---|---|
| Subjects | Upper body | X axis | Y axis | Upper body | X axis | Y axis |
| S32 | 0.974895 | 0.000067 | 0.000204 | 1.011137 | 0.000072 | 0.000215 |
| S33 | 0.877308 | 0.000073 | 0.000134 | 0.899194 | 0.000087 | 0.000196 |
| S34 | 0.867672 | 0.000063 | 0.000127 | 0.894298 | 0.000077 | 0.000188 |
| S35 | 0.948874 | 0.000099 | 0.000182 | 0.952532 | 0.000105 | 0.000217 |
| S36 | 0.968912 | 0.000109 | 0.000217 | 1.020322 | 0.000115 | 0.000240 |
| S37 | 0.811181 | 0.000063 | 0.000204 | 0.964774 | 0.000071 | 0.000244 |
| S38 | 0.921204 | 0.000061 | 0.000160 | 0.966262 | 0.000071 | 0.000213 |
| S39 | 0.907618 | 0.000060 | 0.000151 | 0.951832 | 0.000076 | 0.000188 |
| S40 | 0.907953 | 0.000061 | 0.000169 | 0.920784 | 0.000071 | 0.000188 |
| S41 | 0.907145 | 0.000055 | 0.000151 | 0.937417 | 0.000171 | 0.000196 |
| S42 | 0.909996 | 0.000055 | 0.000163 | 0.995645 | 0.000072 | 0.000222 |
| S43 | 0.940886 | 0.000061 | 0.000137 | 0.971473 | 0.000082 | 0.000188 |
| S44 | 0.979163 | 0.000059 | 0.000127 | 1.058006 | 0.000184 | 0.000244 |
| S45 | 0.946343 | 0.000056 | 0.000109 | 1.029439 | 0.000082 | 0.000156 |
| S46 | 0.951810 | 0.000061 | 0.000154 | 0.977621 | 0.000087 | 0.000256 |
| S47 | 0.809073 | 0.000060 | 0.000147 | 0.961375 | 0.000065 | 0.000252 |
| S48 | 0.961124 | 0.000073 | 0.000176 | 0.997457 | 0.000083 | 0.000189 |
| S49 | 0.994281 | 0.000074 | 0.000172 | 1.020115 | 0.000094 | 0.000222 |
| S50 | 0.853841 | 0.000075 | 0.000194 | 0.978026 | 0.000104 | 0.000247 |
| S51 | 0.818171 | 0.000059 | 0.000168 | 0.850567 | 0.000091 | 0.000255 |
| S52 | 0.845488 | 0.000072 | 0.000134 | 0.895100 | 0.000105 | 0.000293 |
| S53 | 0.899975 | 0.000081 | 0.000150 | 0.967366 | 0.000094 | 0.000179 |
| S54 | 0.819878 | 0.000057 | 0.000106 | 0.907099 | 0.000108 | 0.000193 |
| S55 | 0.824809 | 0.000061 | 0.000119 | 0.854062 | 0.000062 | 0.000125 |
| S56 | 0.829834 | 0.000067 | 0.000126 | 0.915019 | 0.000169 | 0.000157 |
| S57 | 0.836302 | 0.000066 | 0.000126 | 0.892036 | 0.000083 | 0.000172 |
| S58 | 0.876029 | 0.000065 | 0.000155 | 0.988827 | 0.000186 | 0.000163 |
| S59 | 0.876581 | 0.000065 | 0.000149 | 0.924143 | 0.000117 | 0.000296 |
| S60 | 0.881068 | 0.000101 | 0.000252 | 1.063924 | 0.000109 | 0.000381 |
| S61 | 0.880455 | 0.000055 | 0.000093 | 1.007333 | 0.000080 | 0.000190 |
| S62 | 0.900065 | 0.000055 | 0.000087 | 1.028052 | 0.000076 | 0.000176 |
| S63 | 1.045809 | 0.000056 | 0.000102 | 1.061254 | 0.000096 | 0.000161 |
| S64 | 1.067929 | 0.000052 | 0.000105 | 1.070771 | 0.000111 | 0.000162 |
| S65 | 0.949971 | 0.000055 | 0.000101 | 1.004960 | 0.000068 | 0.000143 |
| S66 | 0.964054 | 0.000053 | 0.000093 | 1.068673 | 0.000169 | 0.000140 |
| S67 | 0.828268 | 0.000054 | 0.000082 | 0.886462 | 0.000061 | 0.000117 |
| S68 | 0.922679 | 0.000049 | 0.000079 | 0.945291 | 0.000061 | 0.000102 |
| S69 | 0.946723 | 0.000063 | 0.000112 | 1.069926 | 0.000114 | 0.000119 |
| S70 | 0.977655 | 0.000064 | 0.000113 | 0.999438 | 0.000065 | 0.000119 |
| mean | 0.914217 | 0.000067 | 0.000153 | 0.966343 | 0.000096 | 0.000208 |
| SD | 0.061596 | 0.000014 | 0.000044 | 0.057911 | 0.000033 | 0.000058 |

The time domain index for the cardiac output, HR, BPM, SDNN, rMSSD, and pNN50, were extracted from the pupillary response. These components were compared with the time domain index from the ECG signals (i.e., ground truth).

Figure 7:
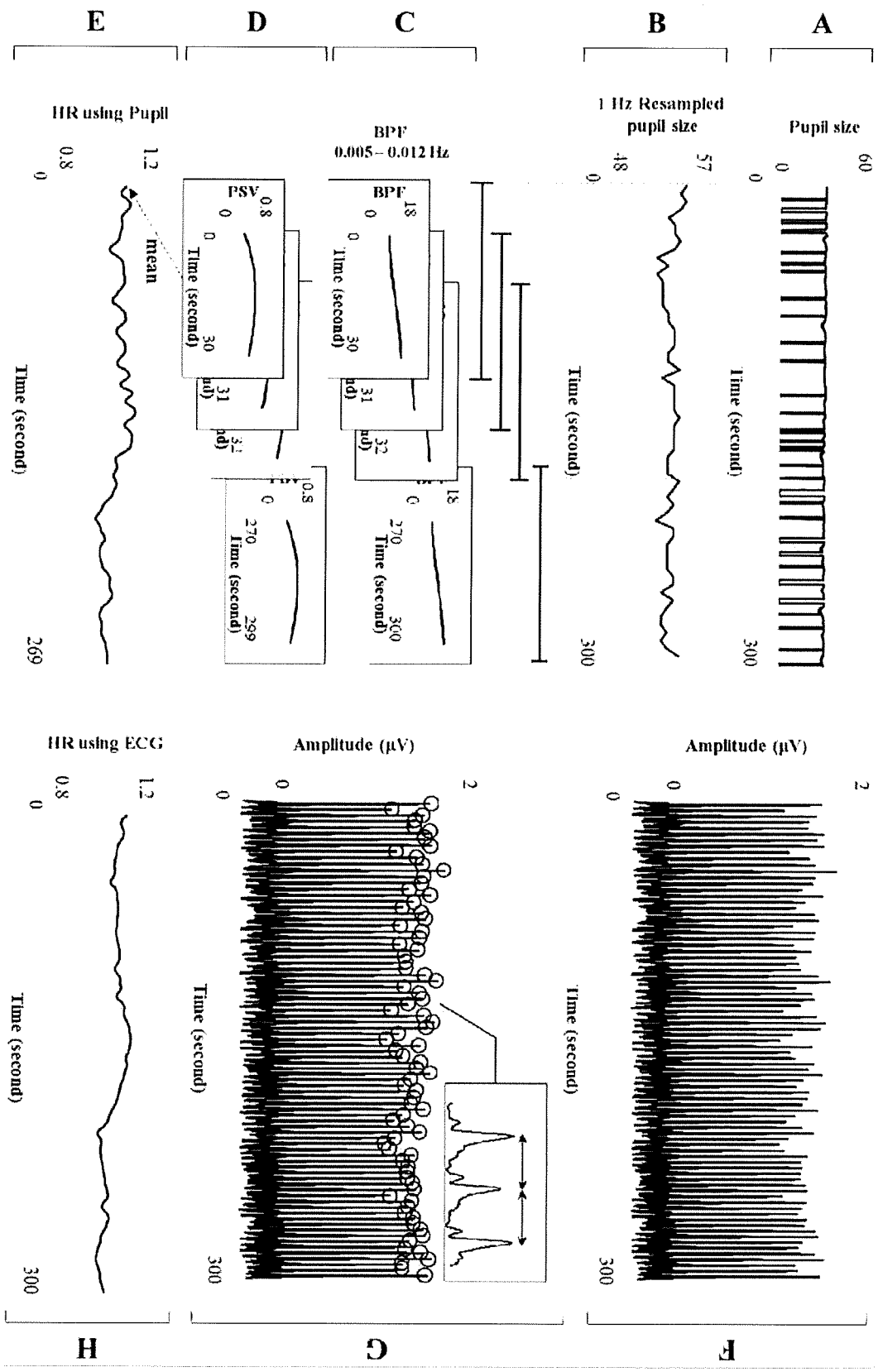
FIG. 7 shows examples of processing for extracting heart rate (HR) from the pupillary response and ECG signals.

The examples for processing for extracting the HR from the pupillary response and ECG signals are shown in FIG. 7. This experiment was able to determine the cardiac time indices, HR, BPM, SDNN, rMSSD, and pNN50 from the pupillary response by the entrainment of the harmonic frequency. The cardiac heart rhythm in the range of 0.5 Hz-1.2 Hz was closely connected to the circadian pupillary rhythm within the range of 0.005 Hz-0.012 Hz. The size variation of the pupil diameter was synchronized with the heart rhythm where the resolution of harmonic frequency band is 1/100 resolution. That is, the frequency range is the same as a harmonic frequency range of 1/100 of the frequency of an ECG signal (ground truth). Other time domain indexes, BPM, SDNN, rMSSD, and pNN50, were calculated from the HR signals.

In FIG. 7, (A) shows frame difference signals of pupil size, (B) shows a wave form by signals of 1 Hz resampled based on sliding moving average (window size: 30 fps and resolution: 30 fps), (C) shows band pass filtered signals of 0.005 Hz-0.012 Hz with harmonic frequency of 1/100f, (D) shows signals of pupil size variation, (E) shows a wave form of heart rate from pupillary response, (F) shows ECG raw signals, (G) shows detecting the R-peak (QRS complex) and R-peak to R-peak intervals from ECG raw signals, and (H) shows a wave form of heart rate from ECG signals (ground truth).

Figure 8:
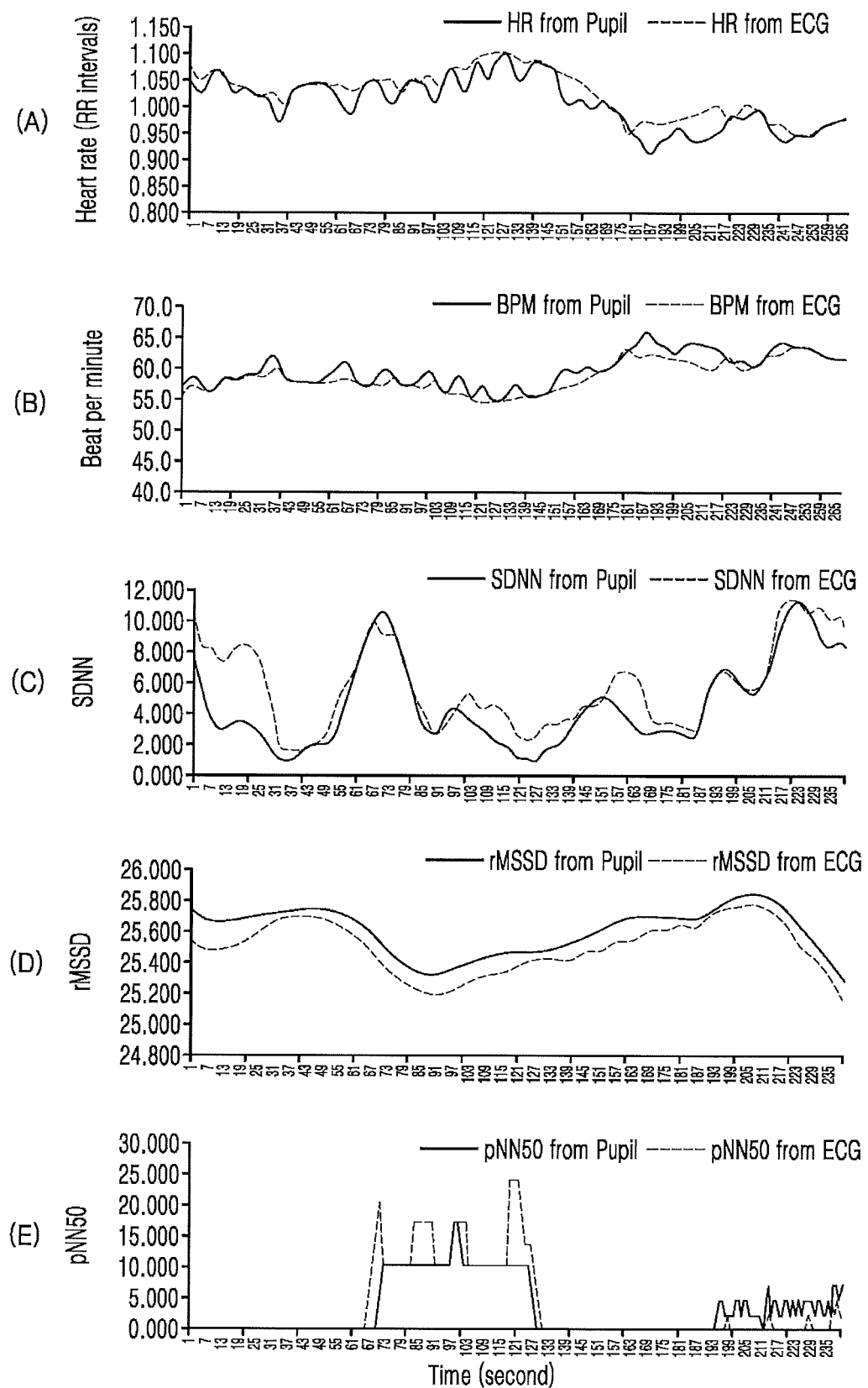
FIG. 8 shows a comparison example of cardiac time indexes, extracted from the pupillary response and ECG signals in movelessness condition (MNC)

FIG. 8 shows a comparison example of cardiac time indexes (HR, BPM, SDNN, rMSSD, and pNN50) in MNC for a subject, where r=0.921, ME=0.018 for HR, r=0.918, ME=1.063 for BPM, r=0.864, ME=1.308 for SDNN, r=0.977, ME=0.100 for rMSSD, r=0.838, ME=1.642 for pNN50.

Comparing the results with the ground truth in the MNC for all subjects, the cardiac time indexes from the pupillary response indicated a strong correlation coefficient (r) for all parameters where r=0.898±0.064 for HR; r=0.898±0.064 for BPM; r=0.783±0.088 for SDNN; r=0.944±0.059 for rMSSD; and r=0.804±0.055 for pNN50. All the differences between the mean error ME of all parameters was low where ME=0.009±0.006 for HR; ME=0.825±0.296 for BPM; ME=3.138±3.453 for SDNN; ME=0.143±0.101 for rMSSD; and ME=1.433±0.346 for pNN50.

This procedure was performed by the sliding window technique where the window size was 30 s and the resolution was 1 s by using the recorded data for 300 s.

Table 4 shows average of correlation coefficient and mean error of cardiac time index in MNC (N=270, p<0.01). In Table 4, the correlation coefficient and mean error are the mean value for 70 subjects (in one subject, N=270).

TABLE 4

| Subjects | Correlation coefficient | | | | | Mean error | | | | |
|---|---|---|---|---|---|---|---|---|---|---|
| | HR | BPM | SDNN | rMSSD | pNN50 | HR | BPM | SDNN | rMSSD | pNN50 |
| S1 | 0.968 | 0.968 | 0.722 | 0.993 | 0.818 | 0.005 | 0.513 | 1.986 | 0.055 | 1.725 |
| S2 | 0.877 | 0.877 | 0.610 | 0.972 | 0.830 | 0.005 | 0.575 | 1.811 | 0.045 | 1.825 |
| S3 | 0.871 | 0.871 | 0.635 | 0.934 | 0.850 | 0.008 | 0.973 | 2.292 | 0.142 | 1.459 |
| S4 | 0.803 | 0.803 | 0.732 | 0.858 | 0.793 | 0.009 | 1.227 | 2.866 | 0.162 | 1.974 |
| S5 | 0.957 | 0.957 | 0.870 | 0.993 | 0.773 | 0.004 | 0.533 | 1.133 | 0.070 | 1.212 |
| S6 | 0.969 | 0.969 | 0.900 | 0.997 | 0.899 | 0.004 | 0.596 | 1.250 | 0.079 | 1.388 |
| S7 | 0.866 | 0.866 | 0.682 | 0.908 | 0.763 | 0.007 | 0.668 | 1.953 | 0.090 | 1.781 |
| S8 | 0.896 | 0.896 | 0.830 | 0.942 | 0.803 | 0.004 | 0.466 | 1.594 | 0.049 | 1.790 |
| S9 | 0.942 | 0.942 | 0.842 | 0.975 | 0.758 | 0.006 | 0.622 | 2.132 | 0.063 | 1.802 |
| S10 | 0.817 | 0.817 | 0.888 | 0.989 | 0.869 | 0.008 | 0.860 | 3.016 | 0.253 | 1.998 |
| S11 | 0.888 | 0.888 | 0.776 | 0.978 | 0.805 | 0.015 | 1.206 | 3.140 | 0.079 | 1.430 |
| S12 | 0.973 | 0.973 | 0.753 | 0.984 | 0.764 | 0.007 | 0.670 | 5.639 | 0.393 | 0.951 |
| S13 | 0.946 | 0.946 | 0.821 | 0.971 | 0.814 | 0.026 | 1.237 | 4.773 | 0.382 | 1.242 |
| S14 | 0.936 | 0.936 | 0.820 | 0.983 | 0.727 | 0.026 | 1.281 | 2.502 | 0.062 | 0.802 |
| S15 | 0.914 | 0.914 | 0.936 | 0.994 | 0.868 | 0.018 | 1.062 | 1.397 | 0.050 | 1.211 |
| S16 | 0.949 | 0.949 | 0.774 | 0.932 | 0.817 | 0.006 | 0.667 | 3.560 | 0.360 | 0.829 |
| S17 | 0.974 | 0.974 | 0.705 | 0.860 | 0.731 | 0.004 | 0.515 | 5.968 | 0.252 | 0.990 |
| S18 | 0.782 | 0.782 | 0.721 | 0.993 | 0.735 | 0.023 | 1.275 | 1.404 | 0.093 | 0.952 |
| S19 | 0.966 | 0.966 | 0.929 | 0.988 | 0.832 | 0.005 | 0.680 | 0.824 | 0.091 | 1.872 |
| S20 | 0.947 | 0.947 | 0.862 | 0.934 | 0.746 | 0.005 | 0.691 | 2.712 | 0.090 | 0.818 |
| S21 | 0.944 | 0.944 | 0.849 | 0.949 | 0.846 | 0.006 | 0.605 | 2.034 | 0.071 | 1.260 |
| S22 | 0.962 | 0.962 | 0.718 | 0.993 | 0.782 | 0.006 | 0.601 | 1.549 | 0.042 | 1.311 |
| S23 | 0.784 | 0.784 | 0.789 | 0.770 | 0.797 | 0.009 | 0.920 | 5.194 | 0.151 | 1.157 |
| S24 | 0.963 | 0.963 | 0.958 | 0.997 | 0.770 | 0.004 | 0.445 | 1.318 | 0.116 | 1.332 |
| S25 | 0.718 | 0.718 | 0.864 | 0.977 | 0.838 | 0.010 | 0.630 | 1.308 | 0.100 | 1.642 |
| S26 | 0.981 | 0.981 | 0.808 | 0.901 | 0.701 | 0.006 | 1.024 | 4.944 | 0.262 | 1.177 |
| S27 | 0.932 | 0.932 | 0.703 | 0.985 | 0.782 | 0.005 | 0.759 | 4.185 | 0.193 | 1.220 |
| S28 | 0.954 | 0.954 | 0.937 | 0.986 | 0.793 | 0.013 | 0.951 | 1.965 | 0.249 | 1.922 |
| S29 | 0.918 | 0.918 | 0.667 | 0.975 | 0.815 | 0.015 | 1.188 | 3.783 | 0.207 | 1.514 |
| S30 | 0.923 | 0.923 | 0.850 | 0.988 | 0.866 | 0.013 | 1.018 | 1.784 | 0.100 | 1.922 |
| S31 | 0.954 | 0.954 | 0.734 | 0.906 | 0.881 | 0.008 | 0.738 | 4.475 | 0.148 | 1.927 |
| S32 | 0.834 | 0.834 | 0.794 | 0.864 | 0.700 | 0.013 | 1.087 | 27.157 | 0.402 | 1.652 |
| S33 | 0.831 | 0.831 | 0.677 | 0.832 | 0.893 | 0.005 | 0.518 | 2.006 | 0.046 | 1.754 |
| S34 | 0.903 | 0.903 | 0.790 | 0.889 | 0.799 | 0.005 | 0.500 | 2.100 | 0.052 | 1.574 |
| S35 | 0.943 | 0.943 | 0.823 | 0.964 | 0.825 | 0.005 | 0.569 | 1.704 | 0.040 | 1.227 |
| S36 | 0.922 | 0.922 | 0.837 | 0.988 | 0.800 | 0.004 | 0.430 | 1.678 | 0.054 | 1.516 |
| S37 | 0.969 | 0.969 | 0.680 | 0.993 | 0.856 | 0.009 | 1.160 | 1.675 | 0.027 | 1.216 |
| S38 | 0.966 | 0.966 | 0.796 | 0.992 | 0.718 | 0.007 | 0.723 | 2.699 | 0.181 | 0.941 |
| S39 | 0.954 | 0.954 | 0.823 | 0.992 | 0.794 | 0.011 | 1.002 | 1.655 | 0.101 | 1.975 |
| S40 | 0.944 | 0.944 | 0.764 | 0.992 | 0.817 | 0.004 | 0.438 | 2.659 | 0.151 | 1.729 |
| S41 | 0.845 | 0.845 | 0.819 | 0.980 | 0.807 | 0.005 | 0.663 | 1.292 | 0.048 | 1.506 |
| S42 | 0.925 | 0.925 | 0.834 | 0.964 | 0.819 | 0.020 | 1.932 | 7.058 | 0.375 | 1.475 |
| S43 | 0.876 | 0.876 | 0.826 | 0.992 | 0.804 | 0.013 | 0.996 | 2.204 | 0.201 | 1.178 |
| S44 | 0.852 | 0.852 | 0.677 | 0.819 | 0.820 | 0.013 | 1.010 | 6.789 | 0.364 | 0.829 |
| S45 | 0.924 | 0.924 | 0.745 | 0.976 | 0.824 | 0.008 | 0.753 | 2.323 | 0.120 | 1.305 |
| S46 | 0.863 | 0.863 | 0.810 | 0.946 | 0.744 | 0.006 | 0.644 | 1.728 | 0.074 | 1.541 |
| S47 | 0.873 | 0.873 | 0.877 | 0.968 | 0.859 | 0.011 | 0.788 | 3.272 | 0.145 | 1.625 |
| S48 | 0.781 | 0.781 | 0.742 | 0.777 | 0.888 | 0.018 | 1.301 | 6.044 | 0.264 | 1.469 |
| S49 | 0.918 | 0.918 | 0.841 | 0.991 | 0.882 | 0.011 | 0.969 | 1.644 | 0.186 | 1.263 |
| S50 | 0.812 | 0.812 | 0.719 | 0.925 | 0.888 | 0.010 | 0.916 | 1.870 | 0.162 | 1.183 |
| S51 | 0.925 | 0.925 | 0.817 | 0.963 | 0.800 | 0.005 | 0.550 | 1.311 | 0.062 | 1.836 |
| S52 | 0.888 | 0.888 | 0.945 | 0.956 | 0.728 | 0.005 | 0.561 | 1.294 | 0.058 | 0.955 |
| S53 | 0.816 | 0.816 | 0.674 | 0.884 | 0.761 | 0.022 | 1.543 | 8.718 | 0.326 | 1.189 |
| S54 | 0.955 | 0.955 | 0.730 | 0.792 | 0.837 | 0.005 | 0.580 | 8.705 | 0.203 | 1.811 |
| S55 | 0.880 | 0.880 | 0.888 | 0.986 | 0.929 | 0.006 | 0.750 | 1.429 | 0.042 | 1.207 |
| S56 | 0.824 | 0.824 | 0.654 | 0.923 | 0.728 | 0.016 | 0.966 | 1.470 | 0.077 | 1.912 |
| S57 | 0.731 | 0.731 | 0.703 | 0.918 | 0.876 | 0.020 | 1.220 | 6.652 | 0.220 | 1.037 |
| S58 | 0.929 | 0.929 | 0.676 | 0.863 | 0.740 | 0.009 | 0.842 | 6.885 | 0.283 | 1.556 |
| S59 | 0.862 | 0.862 | 0.824 | 0.978 | 0.761 | 0.010 | 0.941 | 1.329 | 0.146 | 1.640 |
| S60 | 0.958 | 0.958 | 0.713 | 0.961 | 0.813 | 0.006 | 0.622 | 1.458 | 0.171 | 1.585 |
| S61 | 0.913 | 0.913 | 0.830 | 0.985 | 0.700 | 0.005 | 0.545 | 1.623 | 0.064 | 1.899 |
| S62 | 0.919 | 0.919 | 0.880 | 0.985 | 0.830 | 0.009 | 0.807 | 1.393 | 0.044 | 1.408 |
| S63 | 0.932 | 0.932 | 0.792 | 0.982 | 0.751 | 0.006 | 0.575 | 2.005 | 0.154 | 1.373 |
| S64 | 0.864 | 0.864 | 0.671 | 0.984 | 0.706 | 0.005 | 0.651 | 1.882 | 0.085 | 1.167 |
| S65 | 0.953 | 0.953 | 0.639 | 0.939 | 0.884 | 0.004 | 0.563 | 1.180 | 0.090 | 0.847 |
| S66 | 0.735 | 0.735 | 0.943 | 0.996 | 0.794 | 0.004 | 0.511 | 0.997 | 0.080 | 1.768 |
| S67 | 0.897 | 0.893 | 0.611 | 0.932 | 0.898 | 0.009 | 1.217 | 1.251 | 0.035 | 1.735 |
| S68 | 0.861 | 0.861 | 0.771 | 0.818 | 0.776 | 0.006 | 0.684 | 3.480 | 0.167 | 0.820 |
| S69 | 0.898 | 0.898 | 0.669 | 0.873 | 0.778 | 0.009 | 0.987 | 2.368 | 0.111 | 1.859 |
| S70 | 0.921 | 0.918 | 0.841 | 0.945 | 0.782 | 0.018 | 1.063 | 2.158 | 0.071 | 1.336 |
| mean | 0.898 | 0.898 | 0.783 | 0.944 | 0.804 | 0.009 | 0.825 | 3.138 | 0.143 | 1.433 |
| SD | 0.064 | 0.064 | 0.088 | 0.059 | 0.055 | 0.006 | 0.296 | 3.453 | 0.101 | 0.346 |

Figure 9:
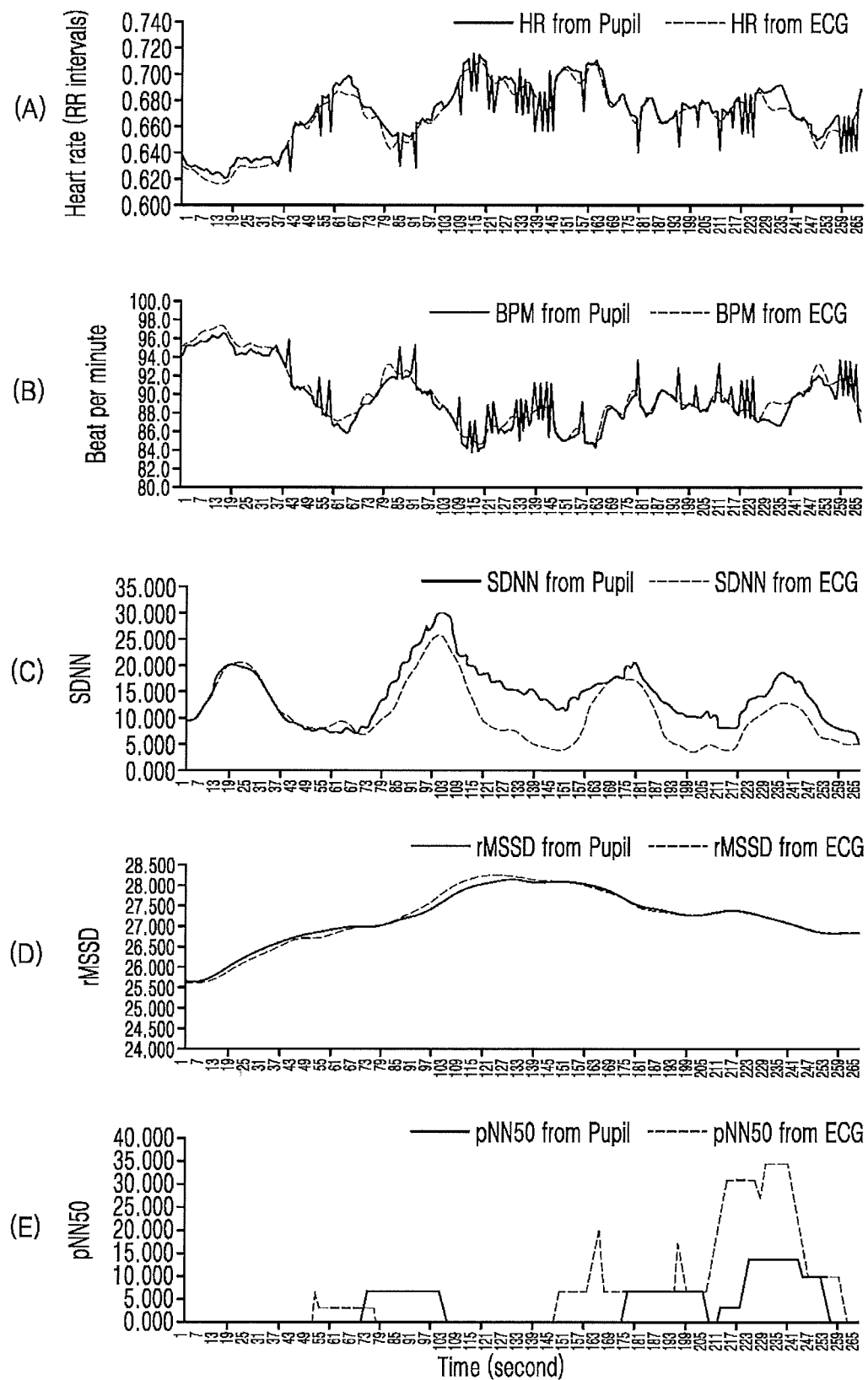
FIG. 9 shows a comparison example of the cardiac time index extracted from the pupillary response and ECG signals in natural movement condition (NMC)

FIG. 9 shows a comparison example of the cardiac time index extracted from the pupillary response and ECG signals (NMC) for a subject, where r=0.915, ME=0.007 for HR, r=0.917, ME=0.934 for BPM, r=0.841, ME=3.763 for SDNN, r=0.996, ME=0.065 for rMSSD, r=0.636, ME=4.957 for pNN50.

Comparing result with ground truth in NMC for all subjects, the cardiac time index from pupillary response were strong correlation of all parameters with r=0.824±0.091 for HR, r=0.824±0.090 for BPM, r=0.710±0.105 for SDNN, r=0.938±0.077 for rMSSD, and r=0.748±0.082 for pNN50. The difference between the mean error of all parameters was low with ME=0.013±0.007 for HR, ME=1.295±0.585 for BPM, ME=4.178±2.501 for SDNN, ME=0.154±0.113 for rMSSD, and ME=1.872±0.979 for pNN50.

This procedure was performed and processed by sliding window technique (window size: 30 s and resolution: 1 s) by using recorded data for 300 s. The correlation and mean error were mean value for 70 subjects (in one subject, N=270), as shown in Table 5.

Table 5 shows average of correlation coefficient and mean error of cardiac time index in NMC (N=270, p<0.01).

TABLE 5

| Subjects | Correlation coefficient | | | | | Mean error | | | | |
| --- | --- | --- | --- | --- | --- | --- | --- | --- | --- | --- |
| | HR | BPM | SDNN | rMSSD | pNN50 | HR | BPM | SDNN | rMSSD | pNN50 |
| S1 | 0.760 | 0.760 | 0.590 | 0.940 | 0.819 | 0.014 | 1.631 | 5.792 | 0.165 | 1.411 |
| S2 | 0.819 | 0.819 | 0.707 | 0.958 | 0.846 | 0.009 | 1.093 | 3.647 | 0.109 | 1.615 |
| S3 | 0.923 | 0.923 | 0.680 | 0.765 | 0.797 | 0.007 | 0.958 | 5.027 | 0.324 | 3.179 |
| S4 | 0.780 | 0.780 | 0.658 | 0.955 | 0.626 | 0.006 | 0.886 | 2.761 | 0.121 | 1.026 |
| S5 | 0.801 | 0.801 | 0.646 | 0.906 | 0.805 | 0.005 | 0.807 | 2.802 | 0.061 | 1.248 |
| S6 | 0.680 | 0.680 | 0.807 | 0.906 | 0.738 | 0.011 | 1.167 | 1.872 | 0.057 | 2.157 |
| S7 | 0.583 | 0.583 | 0.665 | 0.980 | 0.737 | 0.008 | 0.880 | 7.492 | 0.097 | 2.735 |
| S8 | 0.948 | 0.948 | 0.631 | 0.875 | 0.688 | 0.008 | 0.831 | 6.002 | 0.054 | 2.482 |
| S9 | 0.874 | 0.874 | 0.770 | 0.990 | 0.636 | 0.009 | 0.963 | 3.763 | 0.065 | 4.957 |
| S10 | 0.744 | 0.744 | 0.593 | 0.929 | 0.684 | 0.014 | 1.275 | 2.677 | 0.178 | 2.962 |
| S11 | 0.929 | 0.929 | 0.662 | 0.989 | 0.833 | 0.014 | 1.221 | 3.819 | 0.149 | 1.599 |
| S12 | 0.951 | 0.951 | 0.936 | 0.994 | 0.765 | 0.025 | 1.438 | 7.297 | 0.365 | 2.057 |
| S13 | 0.664 | 0.664 | 0.531 | 0.897 | 0.801 | 0.026 | 1.553 | 4.627 | 0.368 | 3.030 |
| S14 | 0.816 | 0.816 | 0.777 | 0.971 | 0.642 | 0.015 | 1.258 | 3.700 | 0.047 | 3.348 |
| S15 | 0.795 | 0.795 | 0.786 | 0.988 | 0.797 | 0.019 | 1.583 | 3.513 | 0.049 | 2.664 |
| S16 | 0.890 | 0.890 | 0.911 | 0.984 | 0.634 | 0.007 | 0.936 | 1.510 | 0.187 | 2.986 |
| S17 | 0.915 | 0.915 | 0.617 | 0.983 | 0.798 | 0.007 | 0.937 | 5.137 | 0.183 | 1.681 |
| S18 | 0.787 | 0.787 | 0.937 | 0.977 | 0.868 | 0.017 | 1.337 | 1.045 | 0.096 | 2.625 |
| S19 | 0.779 | 0.779 | 0.886 | 0.983 | 0.602 | 0.015 | 1.094 | 1.497 | 0.087 | 3.138 |
| S20 | 0.915 | 0.917 | 0.559 | 0.713 | 0.620 | 0.007 | 0.934 | 8.762 | 0.590 | 3.138 |
| S21 | 0.932 | 0.932 | 0.674 | 0.897 | 0.836 | 0.006 | 0.919 | 7.140 | 0.206 | 2.134 |
| S22 | 0.929 | 0.929 | 0.813 | 0.974 | 0.805 | 0.006 | 0.866 | 3.100 | 0.088 | 1.427 |
| S23 | 0.634 | 0.634 | 0.638 | 0.954 | 0.662 | 0.033 | 3.858 | 2.985 | 0.215 | 0.717 |
| S24 | 0.822 | 0.822 | 0.894 | 0.995 | 0.710 | 0.017 | 1.819 | 1.458 | 0.123 | 3.229 |
| S25 | 0.842 | 0.842 | 0.754 | 0.985 | 0.754 | 0.016 | 1.749 | 2.211 | 0.062 | 1.108 |
| S26 | 0.871 | 0.871 | 0.637 | 0.993 | 0.638 | 0.010 | 1.118 | 3.722 | 0.195 | 2.399 |
| S27 | 0.822 | 0.822 | 0.658 | 0.976 | 0.694 | 0.025 | 1.377 | 6.905 | 0.101 | 2.765 |
| S28 | 0.751 | 0.751 | 0.661 | 0.765 | 0.796 | 0.016 | 0.949 | 3.741 | 0.226 | 0.267 |
| S29 | 0.948 | 0.948 | 0.683 | 0.976 | 0.625 | 0.007 | 1.192 | 2.867 | 0.175 | 0.884 |
| S30 | 0.876 | 0.876 | 0.796 | 0.976 | 0.628 | 0.005 | 0.751 | 4.662 | 0.170 | 1.679 |
| S31 | 0.850 | 0.850 | 0.642 | 0.743 | 0.847 | 0.015 | 1.351 | 1.505 | 0.163 | 2.675 |
| S32 | 0.878 | 0.878 | 0.814 | 0.992 | 0.708 | 0.012 | 1.154 | 3.122 | 0.204 | 0.982 |
| S33 | 0.945 | 0.945 | 0.816 | 0.971 | 0.853 | 0.013 | 1.013 | 2.415 | 0.112 | 1.925 |
| S34 | 0.737 | 0.737 | 0.630 | 0.976 | 0.730 | 0.015 | 1.416 | 2.769 | 0.076 | 0.847 |
| S35 | 0.812 | 0.812 | 0.622 | 0.966 | 0.816 | 0.016 | 1.396 | 4.748 | 0.059 | 1.924 |
| S36 | 0.714 | 0.714 | 0.622 | 0.745 | 0.627 | 0.010 | 1.208 | 2.266 | 0.174 | 0.919 |
| S37 | 0.828 | 0.828 | 0.626 | 0.839 | 0.607 | 0.009 | 1.085 | 2.464 | 0.252 | 1.644 |
| S38 | 0.747 | 0.747 | 0.645 | 0.758 | 0.793 | 0.020 | 2.090 | 7.520 | 0.138 | 2.080 |
| S39 | 0.869 | 0.869 | 0.665 | 0.984 | 0.635 | 0.012 | 1.190 | 1.077 | 0.139 | 1.272 |
| S40 | 0.684 | 0.684 | 0.601 | 0.987 | 0.809 | 0.010 | 1.134 | 1.239 | 0.068 | 2.917 |
| S41 | 0.733 | 0.733 | 0.802 | 0.814 | 0.769 | 0.013 | 1.623 | 4.872 | 0.149 | 2.989 |
| S42 | 0.702 | 0.702 | 0.603 | 0.732 | 0.774 | 0.009 | 1.217 | 2.570 | 0.308 | 0.333 |
| S43 | 0.875 | 0.875 | 0.613 | 0.930 | 0.668 | 0.025 | 3.156 | 1.341 | 0.261 | 2.728 |
| S44 | 0.691 | 0.691 | 0.686 | 0.817 | 0.773 | 0.023 | 2.469 | 2.685 | 0.533 | 0.985 |
| S45 | 0.855 | 0.855 | 0.868 | 0.998 | 0.847 | 0.012 | 1.230 | 2.694 | 0.068 | 0.909 |
| S46 | 0.883 | 0.883 | 0.841 | 0.984 | 0.749 | 0.020 | 2.460 | 4.043 | 0.065 | 1.895 |
| S47 | 0.964 | 0.964 | 0.788 | 0.986 | 0.693 | 0.008 | 0.986 | 10.771 | 0.205 | 0.140 |
| S48 | 0.821 | 0.821 | 0.609 | 0.973 | 0.701 | 0.009 | 0.999 | 3.852 | 0.195 | 0.804 |
| S49 | 0.656 | 0.656 | 0.588 | 0.923 | 0.744 | 0.016 | 1.447 | 10.696 | 0.164 | 1.034 |
| S50 | 0.890 | 0.890 | 0.673 | 0.966 | 0.734 | 0.006 | 0.808 | 10.771 | 0.158 | 1.816 |
| S51 | 0.847 | 0.847 | 0.560 | 0.983 | 0.771 | 0.007 | 0.850 | 2.482 | 0.083 | 3.228 |
| S52 | 0.885 | 0.885 | 0.700 | 0.983 | 0.728 | 0.017 | 1.296 | 3.509 | 0.045 | 0.228 |
| S53 | 0.753 | 0.753 | 0.796 | 0.994 | 0.725 | 0.018 | 1.364 | 4.927 | 0.229 | 3.327 |
| S54 | 0.915 | 0.915 | 0.692 | 0.988 | 0.828 | 0.007 | 0.849 | 2.041 | 0.244 | 1.884 |
| S55 | 0.769 | 0.769 | 0.693 | 0.982 | 0.868 | 0.008 | 1.003 | 4.094 | 0.049 | 2.107 |
| S56 | 0.869 | 0.869 | 0.685 | 0.978 | 0.737 | 0.028 | 1.638 | 5.756 | 0.047 | 1.148 |
| S57 | 0.639 | 0.639 | 0.663 | 0.936 | 0.642 | 0.023 | 1.317 | 11.910 | 0.419 | 0.065 |
| S58 | 0.788 | 0.788 | 0.642 | 0.906 | 0.870 | 0.012 | 1.283 | 4.372 | 0.322 | 1.355 |
| S59 | 0.774 | 0.774 | 0.825 | 0.995 | 0.612 | 0.010 | 1.098 | 6.318 | 0.111 | 1.930 |
| S60 | 0.784 | 0.784 | 0.621 | 0.961 | 0.794 | 0.007 | 0.925 | 3.221 | 0.063 | 1.514 |

TABLE 5-continued

| Subjects | Correlation coefficient | | | | | Mean error | | | | |
|---|---|---|---|---|---|---|---|---|---|---|
| | HR | BPM | SDNN | rMSSD | pNN50 | HR | BPM | SDNN | rMSSD | pNN50 |
| S61 | 0.754 | 0.754 | 0.667 | 0.978 | 0.873 | 0.009 | 1.059 | 3.310 | 0.033 | 1.214 |
| S62 | 0.858 | 0.858 | 0.650 | 0.955 | 0.878 | 0.013 | 1.353 | 5.318 | 0.051 | 3.115 |
| S63 | 0.949 | 0.949 | 0.836 | 0.973 | 0.803 | 0.005 | 0.717 | 7.031 | 0.135 | 1.442 |
| S64 | 0.938 | 0.938 | 0.869 | 0.996 | 0.710 | 0.005 | 0.634 | 1.807 | 0.085 | 0.222 |
| S65 | 0.878 | 0.878 | 0.785 | 0.994 | 0.833 | 0.005 | 0.695 | 2.026 | 0.067 | 1.412 |
| S66 | 0.792 | 0.792 | 0.526 | 0.991 | 0.832 | 0.008 | 0.991 | 2.073 | 0.057 | 1.626 |
| S67 | 0.829 | 0.829 | 0.817 | 0.985 | 0.619 | 0.011 | 1.300 | 5.141 | 0.030 | 2.971 |
| S68 | 0.894 | 0.894 | 0.937 | 0.839 | 0.812 | 0.014 | 1.457 | 2.895 | 0.070 | 2.280 |
| S69 | 0.909 | 0.889 | 0.683 | 0.967 | 0.853 | 0.031 | 3.360 | 1.461 | 0.086 | 1.075 |
| S70 | 0.942 | 0.939 | 0.758 | 0.992 | 0.780 | 0.027 | 0.672 | 7.803 | 0.155 | 1.416 |
| mean | 0.824 | 0.824 | 0.710 | 0.938 | 0.748 | 0.013 | 1.295 | 4.178 | 0.154 | 1.872 |
| SD | 0.091 | 0.090 | 0.105 | 0.077 | 0.082 | 0.007 | 0.585 | 2.501 | 0.113 | 0.979 |

Real-Time System for Detecting the Cardiac Time Domain Parameters

The real-time system for detecting information of the cardiac time domain was developed based on capturing and processing of pupil images. This system may include an infrared webcam, near IR (Infra-Red light) illuminator (IR lamp) and personal computer for analysis.

The infrared webcam was divided into two types, the fixed type, which is a common USB webcam, and the portable type, which are represented by wearable devices. The webcam was a HD Pro C920 from Logitech Inc. converted into an infrared webcam to detect the pupil area.

Figure 10:
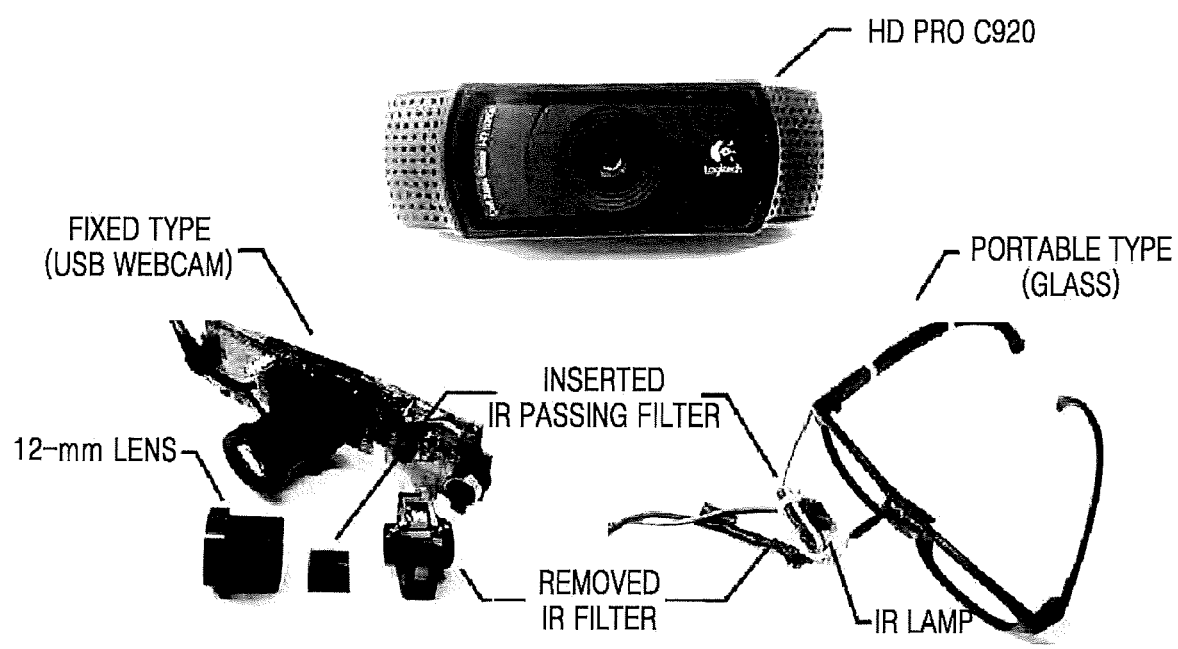
FIG. 10 shows an infrared webcam system for capturing pupil images, according to one or more embodiments.
Figure 10:
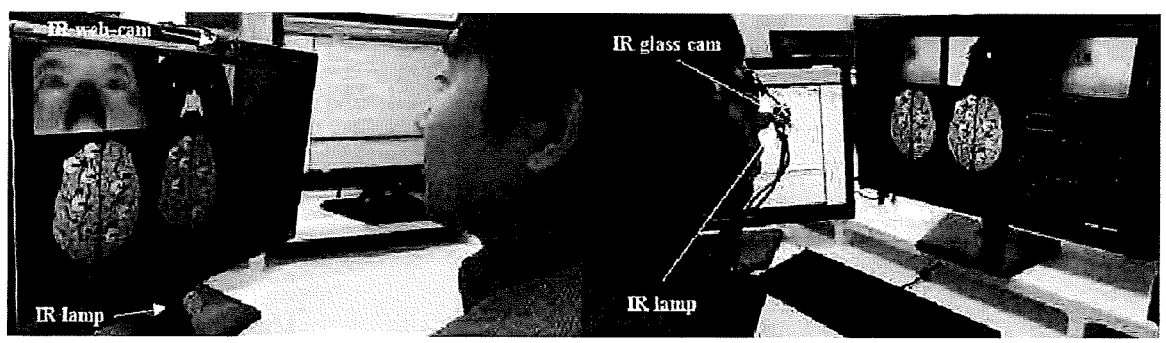

The IR filter inside the webcam was removed and an IR passing filter used for cutting visible light from Kodac Inc., was inserted into the webcam to allow passage of IR wavelength longer than 750 nm, as shown in FIG. 10. The 12-mm lens inside the webcam was replaced with a 3.6-mm lens to allow for focusing on the image when measuring the distance from 0.5 m to 1.5 m.

FIG. 10 shows an infrared webcam system for taking pupil images.

The conventional 12 mm lens of the USB webcam shown in FIG. 12 was replaced with a 3.6 mm lens so that the subject could be focused when a distance of 0.5 m to 1.5 m was photographed.

Figure 11:
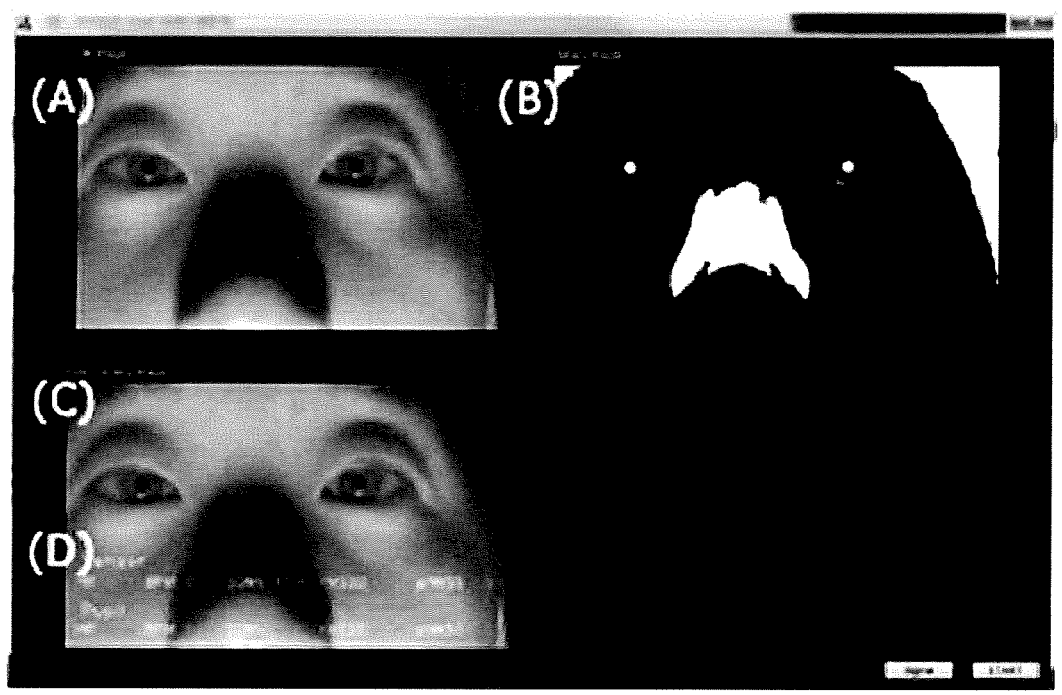
FIG. 11 shows an interface screen of a real-time system, according to one or more embodiments.

FIG. 11 shows an interface screen of a real-time system for detecting and analyzing a biological signal from an infrared webcam and a sensor, where (A): Infrared pupil image (input image), (B): binarized pupil image, (C): Detecting the pupil area, (D): Output of cardiac time parameters.

As described in the above, the present invention develops and provides an advanced method for measurements of human vital signs from moving images of the pupil. Thereby, the measurement of parameters in cardiac time domain can be performed by using a low-cost infrared webcam system that monitored pupillary response. The cardiac time index involved HR and other parameters calculated from it such as BPM, SDNN, rMSSD, and pNN50. This result was verified for both the conditions of noise (MNC and NMC) and various physiological states (variation of arousal and valence level by emotional stimuli of sound) for seventy subjects.

The research for this invention examined the variation in human physiological conditions caused by the stimuli of arousal, relaxation, positive, negative, and neutral moods during verification experiments. The method based on pupillary response according to the present invention is an advanced technique for vital sign monitoring that can measure vital signs in either static or dynamic situations.

The present invention may be applied to various industries such as U-health care, emotional ICT, human factors, HCI, and security that require VSM technology.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of detecting time-domain cardiac information, the method comprising:
   obtaining moving images of a pupil from a subject;
   extracting a pupil size variation (PSV) from the moving images;
   calculating R-peak to R-peak intervals (RRI) in a predetermined frequency range from the PSV; and
   obtaining at least one time-domain cardiac parameter by processing the RRI.

2. The method of claim 1, wherein the predetermined frequency range is a harmonic frequency range of 1/100 of the frequency range of an electrocardiogram (ECG) signal obtained by sensors.

3. The method of claim 2, wherein the predetermined frequency range is between 0.005 Hz-0.012 Hz.

4. The method of claim 2, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

5. The method of claim 3, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

6. The method of claim 1, wherein the predetermined frequency range is between 0.005 Hz-0.012 Hz.

7. The method of claim 6, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

8. The method of claim 1, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

9. A system adopting the method of claim 1, the system comprising:
   a video capturing unit configured to capture the moving images of the subject; and
   a computer system including software for performing the method of claim 1, the computer system being configured to process and analyze the moving images and calculate the at least one cardiac parameter.

10. The system of claim 9, wherein the predetermined frequency range is a harmonic frequency range of $1/100$ of the frequency range of an ECG signal obtained by sensors.

11. The system of claim 10, wherein the predetermined frequency range is between 0.005 Hz-0.012 Hz.

12. The system of claim 10, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

13. The system of claim 11, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

14. The system of claim 9, wherein the predetermined frequency range is between 0.005 Hz-0.012 Hz.

15. The system of claim 14, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

16. The system of claim 9, wherein the at least one cardiac parameter is one of Heart Rate (HR), Standard Deviation of the normal to normal (SDNN), square root of the mean of the squares of successive normal RR intervals (rMSSD) and pNN50 (successive normal RR intervals>50 ms).

* * * * *